(12) United States Patent
Negiz et al.

(10) Patent No.: US 10,214,464 B2
(45) Date of Patent: Feb. 26, 2019

(54) STEADY STATE HIGH TEMPERATURE REACTOR

(71) Applicant: UOP LLC, Des Plaines, IL (US)

(72) Inventors: Antoine Negiz, Wilmette, IL (US);
Robert B. James, Northbrook, IL (US);
Carl J. Stevens, Lake Forest, IL (US);
Donald L. Mittendorf, Phoenix, AZ (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/586,701

(22) Filed: May 4, 2017

(65) Prior Publication Data

US 2017/0233310 A1 Aug. 17, 2017

Related U.S. Application Data

(62) Division of application No. 13/947,519, filed on Jul. 22, 2013, now Pat. No. 9,689,615.

(60) Provisional application No. 61/691,372, filed on Aug. 21, 2012.

(51) Int. Cl.
| | | |
|---|---|---|
| *B01J 3/04* | (2006.01) | |
| *C07C 2/78* | (2006.01) | |
| *F27D 1/00* | (2006.01) | |
| *F27D 1/12* | (2006.01) | |
| *B01J 19/02* | (2006.01) | |
| *B01J 19/26* | (2006.01) | |

(52) U.S. Cl.
CPC ............... *C07C 2/78* (2013.01); *B01J 3/048* (2013.01); *B01J 19/02* (2013.01); *B01J 19/26* (2013.01); *F27D 1/0006* (2013.01); *F27D 1/12* (2013.01); *B01J 2219/00094* (2013.01); *B01J 2219/0218* (2013.01); *B01J 2219/0277* (2013.01)

(58) Field of Classification Search
CPC .................................. C10H 19/00; B01J 19/26
USPC ................................................................ 48/2
See application file for complete search history.

(56) References Cited

U.S. PATENT DOCUMENTS

| | | | | | |
|---|---|---|---|---|---|
| 2,985,698 | A | * | 5/1961 | Pechtold ................... | C07C 4/04 585/324 |
| 3,408,417 | A | * | 10/1968 | Toru Sogawa ............ | C07C 4/04 585/541 |
| 3,414,247 | A | * | 12/1968 | Sama ........................ | F28C 3/06 261/118 |
| 3,563,709 | A | * | 2/1971 | Staud ........................ | C10G 9/36 422/208 |
| 3,865,581 | A | * | 2/1975 | Sekino ................... | C22C 19/058 420/36 |
| 4,136,015 | A | * | 1/1979 | Kamm ..................... | B01J 19/26 208/129 |
| 4,278,446 | A | * | 7/1981 | Von Rosenberg, Jr. ...................... | C10J 3/485 252/373 |
| 4,582,678 | A | * | 4/1986 | Niino ........................ | B22F 7/06 29/423 |

(Continued)

*Primary Examiner* — Matthew J Merkling (57) ABSTRACT

A reactor comprising a thermal barrier surrounding a combustion zone. The reactor further comprises a cooling jacket inner wall and a binder disposed between the cooling jacket inner wall and the thermal barrier, and a cooling jacket outer wall, wherein the cooling jacket inner wall and the cooling jacket outer wall define a cooling channel. The reactor further comprises an outer reactor wall disposed over the cooling jacket outer wall, wherein the outer reactor wall is impermeable and is configured to contain high pressure gas within the reactor.

11 Claims, 6 Drawing Sheets

(56) References Cited

U.S. PATENT DOCUMENTS

| | | | | |
|---|---|---|---|---|
| 4,708,828 A * | 11/1987 | Plannerer | F02M 3/12 | 261/121.3 |
| 4,724,272 A * | 2/1988 | Raniere | C10G 9/38 | 208/129 |
| 4,762,168 A * | 8/1988 | Kawabe | F28B 11/00 | 165/11.1 |
| 5,219,530 A * | 6/1993 | Hertzberg | G10K 15/043 | 208/128 |
| 5,248,408 A * | 9/1993 | Owen | B01J 8/0055 | 208/113 |
| 5,259,856 A * | 11/1993 | Ohga | C03B 37/01446 | 65/423 |
| 5,324,904 A * | 6/1994 | Cresswell | B01J 19/0013 | 219/618 |
| 5,531,066 A * | 7/1996 | Pfefferle | F02C 7/264 | 431/268 |
| 5,565,393 A * | 10/1996 | Felix | B01J 19/02 | 422/241 |
| 5,615,627 A * | 4/1997 | Marr, Jr. | C10B 53/00 | 110/236 |
| 5,720,163 A * | 2/1998 | Pfefferle | F01N 3/18 | 431/7 |
| 5,873,950 A * | 2/1999 | Ganesan | C22C 19/053 | 148/206 |
| 6,134,785 A * | 10/2000 | Walter | B23P 15/008 | 29/890.054 |
| 6,217,286 B1 * | 4/2001 | Huang | B22D 27/045 | 148/404 |
| 6,699,604 B1 * | 3/2004 | Li | C04B 41/009 | 156/89.27 |
| 7,150,931 B1 * | 12/2006 | Jaffrey | H01M 8/0204 | 429/465 |
| 8,636,958 B2 * | 1/2014 | Salazar-Guillen | B01J 19/26 | 422/129 |
| 2001/0001897 A1 * | 5/2001 | Zhao | B23P 15/04 | 29/889 |
| 2001/0014436 A1 * | 8/2001 | Lemelson | F23N 1/022 | 1/22 |
| 2002/0025272 A1 * | 2/2002 | Witherspoon | B22F 3/087 | 419/66 |
| 2002/0056548 A1 * | 5/2002 | Nakamura | B24B 57/02 | 165/154 |
| 2002/0128161 A1 * | 9/2002 | Wickham | C10G 9/16 | 508/541 |
| 2002/0192494 A1 * | 12/2002 | Tzatzov | C23C 26/00 | 428/655 |
| 2003/0010035 A1 * | 1/2003 | Farmer | C23C 4/00 | 60/752 |
| 2003/0236312 A1 * | 12/2003 | O'Rear | C01B 3/02 | 518/728 |
| 2004/0011439 A1 * | 1/2004 | Corrigan | C22C 19/056 | 148/555 |
| 2004/0018144 A1 * | 1/2004 | Briscoe | C01B 3/323 | 423/652 |
| 2005/0058851 A1 * | 3/2005 | Smith | B21C 23/22 | 428/685 |
| 2005/0120981 A1 * | 6/2005 | Ferguson | F24H 1/40 | 122/367.3 |
| 2006/0038044 A1 * | 2/2006 | Van Steenkiste | B05B 7/1486 | 239/594 |
| 2006/0104878 A1 * | 5/2006 | Chiu | F23G 5/50 | 423/240 R |
| 2006/0216429 A1 * | 9/2006 | Bengtsson | C23C 4/06 | 427/446 |
| 2007/0144622 A1 * | 6/2007 | Flahaut | C22C 19/053 | 148/419 |
| 2007/0163749 A1 * | 7/2007 | Miyahara | H01L 23/473 | 165/80.3 |
| 2007/0217995 A1 * | 9/2007 | Matsumura | C25B 1/04 | 423/657 |
| 2007/0235110 A1 * | 10/2007 | Yoshinari | C22C 19/057 | 148/428 |
| 2007/0260101 A1 * | 11/2007 | Carrera | B01D 53/228 | 585/654 |
| 2008/0033221 A1 * | 2/2008 | Hori | B01J 23/44 | 585/273 |
| 2008/0093583 A1 * | 4/2008 | van den Oosterkamp | B01J 8/025 | 252/373 |
| 2009/0000184 A1 * | 1/2009 | Garwood | B01F 7/00875 | 44/307 |
| 2009/0211255 A1 * | 8/2009 | Simons | F23R 3/18 | 60/737 |
| 2009/0283451 A1 * | 11/2009 | Srinivas | C07C 4/04 | 208/48 AA |
| 2010/0020848 A1 * | 1/2010 | Nazmy | C22C 19/057 | 374/179 |
| 2010/0199559 A1 * | 8/2010 | Hallett | B01J 4/005 | 48/127.7 |
| 2010/0216079 A1 * | 8/2010 | Targoff | F23D 11/441 | 431/8 |
| 2010/0290978 A1 * | 11/2010 | Chun | B01J 4/002 | 423/445 R |
| 2010/0314788 A1 * | 12/2010 | Hung | B01J 2/003 | 264/5 |
| 2011/0083435 A1 * | 4/2011 | Palmer | F23D 1/00 | 60/650 |
| 2011/0289842 A1 * | 12/2011 | Oldenburg | C10J 3/485 | 48/61 |
| 2011/0300357 A1 * | 12/2011 | Witz | C23C 4/02 | 428/213 |
| 2012/0023823 A1 * | 2/2012 | D'Agostini | F23G 5/12 | 48/197 R |
| 2012/0117976 A1 * | 5/2012 | Krull | F02C 7/264 | 60/776 |
| 2013/0041050 A1 * | 2/2013 | Luzenski | B01J 19/0093 | 518/706 |
| 2014/0116669 A1 * | 5/2014 | Li | F28F 3/02 | 165/185 |

* cited by examiner

STEADY STATE HIGH TEMPERATURE REACTOR

CROSS-REFERENCE TO RELATED APPLICATIONS

This application is a Division of copending application Ser. No. 13/947,519 filed Jul. 22, 2013, which application claims priority from Provisional Application No. 61/691,372 filed Aug. 21, 2012, the contents of which cited applications are hereby incorporated by reference in their entirety.

FIELD OF THE INVENTION

The disclosure relates in general to a reactor capable of maintaining high reaction temperatures for an extended period of time. In some embodiments, the disclosure relates to a reactor having cooled sidewalls to cool the reactor body while maintaining high reaction temperatures for an extended period of time.

BACKGROUND OF THE INVENTION

High temperature thermal processing techniques are commonly used to convert hydrocarbon feedstock material to more valuable products. Depending on the feedstock material and desired products, some processes require high temperatures to trigger the desired reactions. For example, high temperatures are used to crack various hydrocarbons into lighter products.

In other processes, high temperatures are required both to trigger the desired reactions as well as to provide the enthalpy necessary for formation of the desired products. For example, various thermal processing techniques are used to convert methane directly to $C_2$ hydrocarbons, such as acetylene via reaction (1), ethylene via reaction (2), and ethane via reaction (3).

$$2CH_4 \rightarrow C_2H_2 + 3H_2 \quad (1)$$

$$2CH_4 \rightarrow C_2H_4 + 2H_2 \quad (2)$$

$$2CH_4 \rightarrow C_2H_6 + H_2 \quad (3)$$

These reactions are highly endothermic, requiring approximately 377 kJ/mol, 202 kJ/mol, and 65 kJ/mol, respectively. In addition, higher temperatures are required to achieve high conversion of the feedstock and high selectivity to the desired product.

One type of thermal processing used in the prior art involves exposing the feedstock to high temperature combustion gases causing the feedstock to pyrolyze into the desired unsaturated product. Many traditional processes involve steam cracking, while other processes involve combustion.

The formation of acetylene from methane by thermal processing is difficult because of the relative free energies of formation of methane and acetylene. Above 800 K, $C_xH_y$ compounds may undergo decomposition into carbon and hydrogen. Below 1500 K, the free energy of formation of methane is above that of acetylene. As such, the formation of methane, the final product of thermodynamic equilibrium, is favored over acetylene between the temperatures of 800 K and 1500 K. Above 1500 K, however, the free energy of formation of acetylene is lower than that of methane. As a result, the formation of acetylene is favored over that of methane. But, as the reactants are cooled below 1500 K, the thermodynamic equilibrium shifts back to methane and the acetylene produced at the higher temperature will decompose and reform as methane. Acetylene and the other hydrocarbons can continue to react to form aromatic and polyaromatic species. When water and carbon dioxide are present acetylene can react to form carbon monoxide which is less valuable product than acetylene. Methane is a very refractory material and as such the pyrolitic reaction of methane to form acetylene and other desired hydrocarbons has a high activation energy. The decomposition reactions of acetylene have lower activation energy and thus the formation of acetylene is favored by reacting at high temperatures but with short controlled residence times that minimize consecutive reactions of acetylene with additional acetylene, hydrocarbons and oxygen containing species such as $H_2O$, $CO_2$ and $O_2$. As such, the conversion of methane to acetylene in this manner necessarily requires processing at high temperatures.

Prior art reactors, however, can operate for only short periods of time before components of the reactor are adversely affected by the high temperatures. As such, these reactors can fail prematurely or require excessive maintenance or shutdowns. For large-scale production, however, it is desirable to operate reactors continuously for long periods of time on the order of months, or longer.

Accordingly, it would be an advance in the state of the art to provide a pyrolitic reactor having a cooling means that enables sustained, high-temperature, steady state operation, for a prolonged period of time.

SUMMARY OF THE INVENTION

A reactor is disclosed, wherein the reactor comprises a thermal barrier surrounding a combustion zone. The reactor further comprises a cooling jacket inner wall and a binder disposed between the cooling jacket inner wall and the thermal barrier, and a cooling jacket outer wall, wherein the cooling jacket inner wall and the cooling jacket outer wall define a cooling channel. The reactor further comprises an outer reactor wall disposed over the cooling jacket outer wall, wherein the outer reactor wall is impermeable and is configured to contain high pressure gas within the reactor.

A pyrolytic reactor is disclosed, wherein the pyrolitic reactor comprises a fuel injection zone, a combustion zone adjacent to said fuel injection zone, an expansion zone adjacent to said combustion zone and configured to accelerate a carrier stream to supersonic speed, a feedstock injection zone adjacent to said expansion zone, a feedstock injection zone, a mixing zone adjacent to the feedstock injection zone, and a reaction zone adjacent to said mixing zone.

The pyrolitic reactor further comprises a thermal barrier surrounding the combustion zone, the expansion zone, and the fuel injection zone. The pyrolitic reactor further comprises a cooling jacket inner wall and a binder disposed between the cooling jacket inner wall and the thermal barrier, and a cooling jacket outer wall, wherein the cooling jacket inner wall and the cooling jacket outer wall define a cooling channel. The pyrolitic reactor further comprises an outer reactor wall disposed over the cooling jacket outer wall, wherein the outer reactor wall is impermeable and is configured to contain high pressure gas within the reactor.

A method to form a two carbon alkyne, a two carbon alkene, and/or a two carbon alkane from methane using Applicants' reactor is disclosed. A method to form a two carbon alkyne, a two carbon alkene, and/or a two carbon alkane from methane using Applicants' pyrolitic reactor is disclosed.

DETAILED DESCRIPTION OF THE INVENTION

Conversion of methane to acetylene can be accomplished by thermal processing. The methane feedstock is heated to a temperature at which the formation of acetylene is thermodynamically favored over that of methane. Additional energy must be provided to the reaction mixture to satisfy the endothermic reaction for the formation of acetylene. After a residence time sufficient to result in the desired acetylene formation, the reaction mixture is quickly quenched to freeze the reaction in order to prevent the acetylene from cracking into hydrogen and carbon and reforming as methane.

The described features, structures, or characteristics of the invention may be combined in any suitable manner in one or more embodiments. In the following description, numerous specific details are recited to provide a thorough understanding of the embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In some embodiments related to the production of acetylene, a fuel and oxidizer are combusted to create a high temperature (e.g., >1500 K) and high speed (e.g., >Mach 1) combustion gas stream, in order to favor acetylene formation. Next, a sufficient amount of reaction enthalpy is provided to satisfy the 377 kJ/mol required for the formation of acetylene. If additional energy is not provided, the endothermic nature of the acetylene formation may drive the temperature below 1500 K. Finally, the reaction mixture is quickly cooled at a rate faster than the rate at which the acetylene can decompose into heavier hydrocarbons such as monovinylacetylene, aromatic and polyaromatic species, tar and soot. This quick cooling process is sometimes referred to as "quenching" the reaction when the amount of acetylene is high. It is desirable to initiate the freezing step at the stage of maximum acetylene formation (i.e., the point of thermodynamic equilibrium) and to complete the quenching step as quickly as possible to prevent the decomposition of any acetylene.

While the present disclosure relates to a cooling system incorporated in a reactor used for the pyrolytic conversion of a methane feedstock to acetylene, those skilled in the art will appreciate that the apparatus and methods disclosed herein can be used with other types of high temperature reactors used with other feedstock and to create other products, such as without limitation, dehydrogenation processes resulting in olefins, reforming processes resulting in hydrogen and carbon-containing molecules, such as CO and/or aromatics, and other processes involving endothermic reactions.

Figure 1:
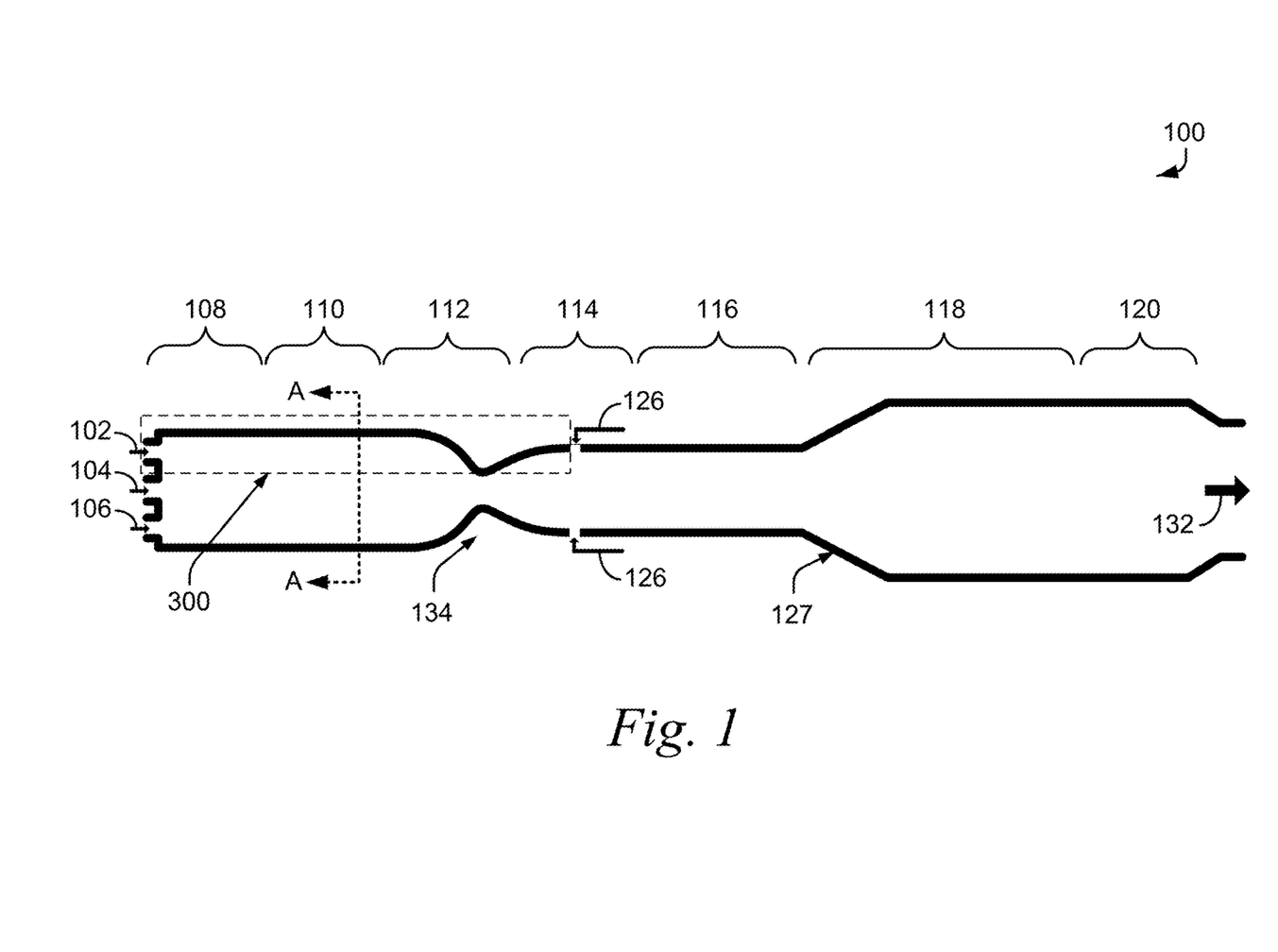
FIG. 1 is a longitudinal cross section of an exemplary pyrolitic reactor.

Referring to FIG. 1, a longitudinal cross section of an exemplary pyrolytic reactor 100 is depicted. In certain embodiments the transverse cross section is circular. The high temperatures necessary for the formation of acetylene as well as controlled residence time and rapid quenching can be achieved in a pyrolytic reactor 100. Fuel 102 and an oxidizer 106 are injected in the fuel injection zone 108 at the proximal end of reactor 100. In certain embodiments, the fuel comprises hydrogen, the oxidizer comprises oxygen, and the ratio of hydrogen to oxygen is greater than about a 2/1 molar ratio. In another embodiment the fuel and oxygen are fed in a ratio so that amount of oxygen is less than the amount required for complete combustion of the fuel.

In some embodiments, the fuel 102 and oxidizer 106 are mixed prior to injection into the fuel injection zone 108. In some embodiments, the fuel 102 and oxidizer 106 are injected into the fuel injection zone 108 and mixed by the turbulent conditions within the fuel injection zone 108.

In some embodiments, a carrier gas 104 is also injected into the fuel injection zone 108 to act as the bulk of the combustion gas stream. In various embodiments, the carrier gas 104 comprises water, a hydrocarbon, hydrogen, $CO_2$, CO, a promoter (such as an acid, base, or surfactant), corrosion inhibitors, a low reactivity fluid (such as nitrogen or a noble gas), or combinations thereof.

The fuel and oxidizer are combusted in the combustion zone 110, and the resulting combustion gas is heated to a high temperature. In some embodiments, the temperature of the combustion gas reaches up to about 3100 K in the combustion zone 110. In other embodiments, the temperature of the carrier gas reaches up to about 3600 K in the combustion zone 110.

The combustion zone 110 is operated at a pressure that is higher than the reactor, which propels the combustion gas toward the distal end of the reactor 100 at high velocity. In some embodiments, the velocity of the combustion gas at the distal end of the combustion zone 110 is below supersonic speed (i.e., less than Mach 1).

The subsonic combustion gas enters the expansion zone 112 and flows through a convergent-divergent nozzle 134. The convergent-divergent nozzle 134 transforms a portion of the thermal energy in the combustion stream into kinetic energy, resulting in a sharp increase in velocity of the combustion stream. The velocity of the combustion stream transitions from subsonic (i.e., less than Mach 1) to supersonic (i.e., greater than Mach 1) within the expansion zone 112. In certain embodiments, at the distal end of the expansion zone 112, the temperature of the combustion gas is 1500 K to 2500 K and in another embodiment the temperature of the combustion gas is less than 3000 K. In certain embodiments, at the distal end of the expansion zone 112, the average velocity of the combustion gas (across a transverse cross section) is greater than Mach 1. In certain embodiments, the average velocity of the combustion gas is about Mach 2 or above.

The methane feedstock is injected into the supersonic combustion gas in the feedstock injection zone 114. In certain embodiments, the feedstock is injected at a temperature of 700 K to 1200 K. In certain embodiments the feedstock is injected at a temperature of 300 K to 2000 K. In certain embodiments, feed lines 126 supply the feedstock.

The combined combustion gas/feedstock stream enters mixing zone 116 where the combined stream is mixed as a result of the turbulent flow in the stream. In certain embodiments the mixing of the combined combustion gas/feedstock is enhanced by shocktrains (a series of oblique shocks occurring in the mixer).

In certain embodiments the diameter of the transverse cross section of the reactor 100 increases in the reactor zone 118 due to angled wall 127. The mixed stream enters the reactor zone 118 and expands into the larger area resulting in a decrease in velocity of the mixed stream.

In some embodiments, the velocity of the mixed stream remains at supersonic velocities within the reaction zone 118. The reduction in velocity of the combustion gas stream converts a portion of the kinetic energy of the stream into thermal energy. The product mixture is then reduced to subsonic flow and quenched in quenching zone 120.

In some embodiments, the velocity of the mixed stream transitions from supersonic to subsonic within the reaction zone 118. At this transition point, a shockwave is formed, which results in a nearly instantaneous increase in the pressure and temperature of the mixed stream. In various embodiments, the temperature of the mixed stream immediately upstream of the shock wave is about 1500 K to 1800 K, as compared to about 2300 K to 2800 K immediately downstream of the shockwave. The conditions in the mixed stream downstream of the shockwave are favorable to the formation of acetylene.

In some embodiments, a shock train is formed at the point where the stream transitions from supersonic to subsonic flow. A shock train is a series of weak shock waves that propagate downstream from the supersonic to subsonic transition point. Whereas a single shockwave will heat the mixture nearly instantaneously (at the location of the shockwave), a shock train will heat the mixture more gradually. Each shock wave in the shock train will increase the temperature of the stream.

The temperature of the mixed stream is increased to favor the formation of acetylene and to provide enough energy to satisfy the endothermic reaction.

In certain embodiments, the product stream exits the reaction zone 118 and enters the quenching zone 120 to rapidly cool the product stream. In certain embodiments, the quenching zone 118 comprises at least one injection nozzle to spray the product stream with water. The product stream is removed at 132.

Figure 2:
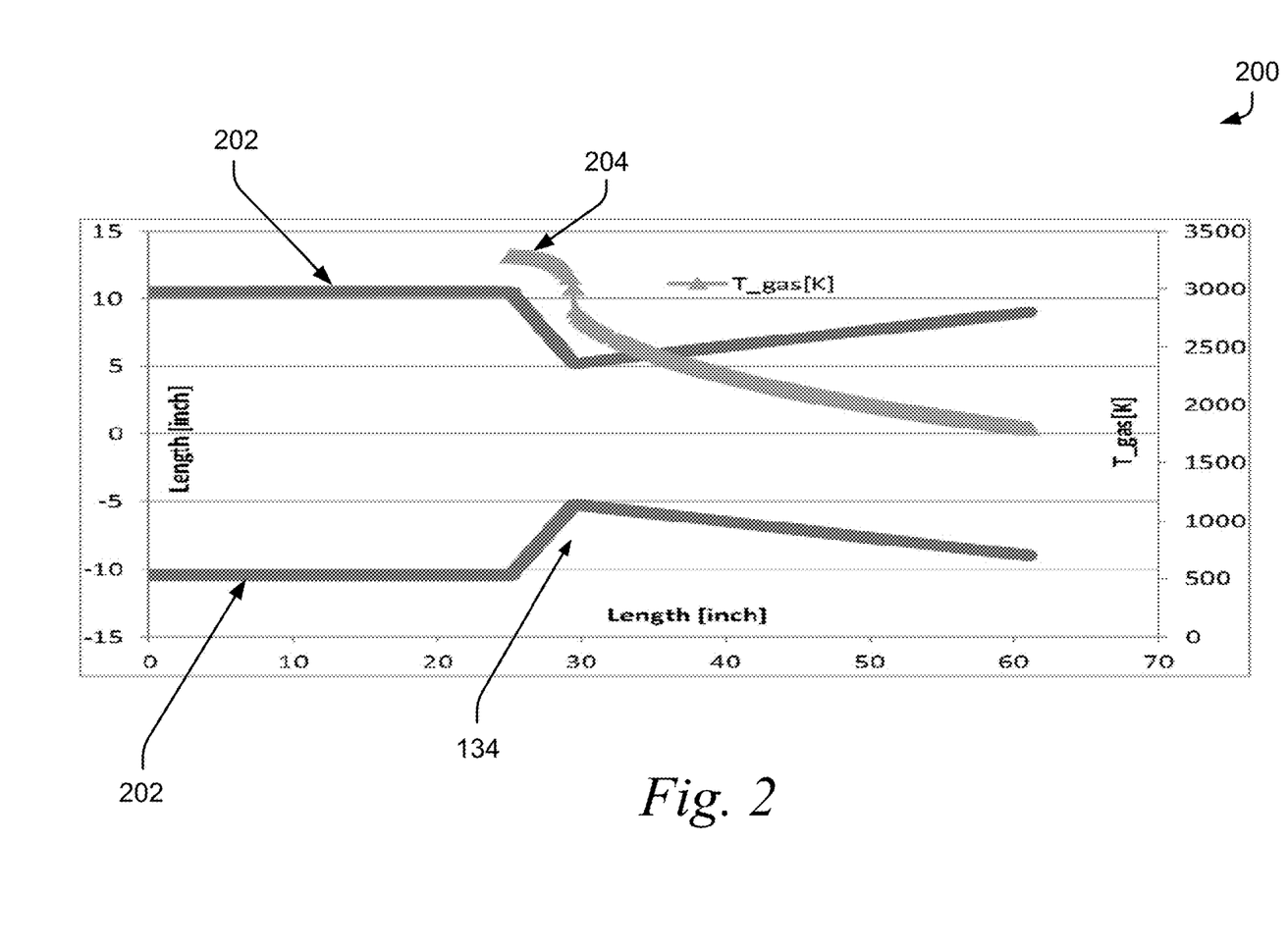
FIG. 2 is a graph of the temperature profile of the exemplary pyrolitic reactor of FIG. 1.

Referring to FIG. 2, a graph 200 of the temperature profile of the exemplary pyrolytic reactor of FIG. 1 is depicted. The walls 202 of the combustion zone 110 and the expansion zone 112 of reactor 100 are shown. The temperature 204 in the combustion zone, ahead of the convergent-divergent nozzle 134, is about 3300 K. As the stream travels through the converging-diverging nozzle 134, the thermal energy is converted to kinetic energy. As a result, the temperature of the stream drops while the velocity of the stream increases to supersonic speeds. In order to maintain steady state operation of the reactor 10 over a long period of time, the combustion portion is cooled as further described below. In various embodiments, the reactor described herein is capable of operating at steady state conditions for at least 24 hours.

Figure 3:
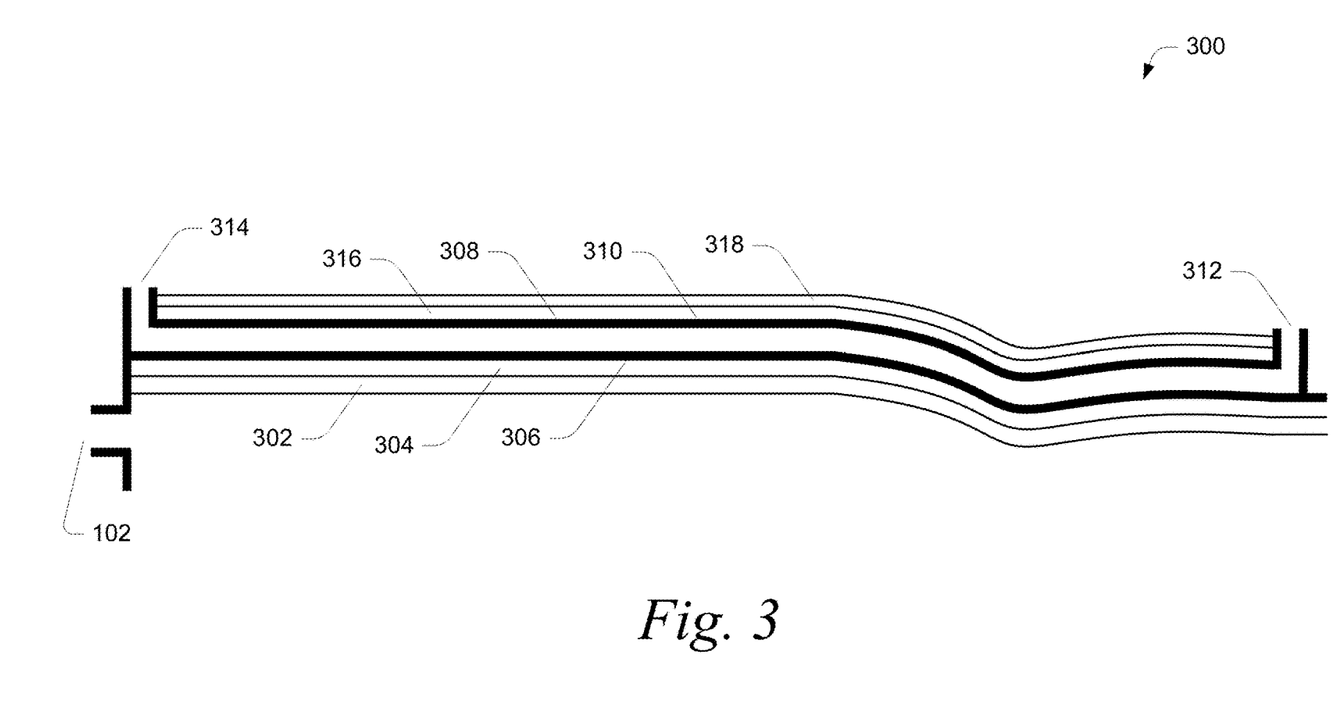
FIG. 3 is a detailed view of a portion of the exemplary pyrolitic reactor of FIG. 1.

Referring to FIG. 3, a detailed view of a portion 300 of the reactor 100 of FIG. 1 is depicted. The portion 300, which includes the fuel injection zone 108, the combustion zone 110, and the expansion zone 112, is indicated by the dashed box in FIG. 1. The portion 300 includes an outer reactor wall 316. In certain embodiments the outer reactor wall is impermeable and is designed to contain the high pressure gas in the reactor either under normal operation or as secondary containment. In certain embodiments the outer reactor wall is made of metal and is thicker than 0.5 inches. The portion 300 includes an inner cooling jacket which in certain embodiments is composed of a plurality of cooling channels. In certain embodiments the cooling jacket is composed of an outer cooling channel wall 308 which can be fabricated from a different metal than the outer reactor wall. In another embodiment the outer reactor wall serves as the outer cooling channel wall. In certain embodiments the cooling jacket is composed of an inner cooling channel wall 306. The interior of portion 300 is lined with a thermal barrier 302.

In certain embodiments, the thermal barrier 302 has a thermal conductivity between about 0.1 $W \cdot m^{-1} \cdot K^{-1}$ to about 10 $W \cdot m^{-1} \cdot K^{-1}$. In certain embodiments, the thermal barrier 302 is any material with a thermal conductivity of about 10 $W \cdot m^{-1} \cdot K^{-1}$. In certain embodiments, the thermal barrier has a thermal conductivity of about 1 $W \cdot m^{-1} \cdot K^{-1}$.

In certain embodiments, the thermal barrier has a thickness between about 0.25 mm (0.01 inches) to about 1.52 mm (0.06 inches).

Materials with good high temperature resistance to reducing, oxidizing and hydrothermal environments are preferred.

In various embodiments, the thermal barrier is formed by electron beam physical vapor deposition (PVD), air plasma spraying (APS), high velocity oxygen fuel thermal spraying (HVOF), electrostatic spray assisted vapor deposition (ES-AVD), directed vapor deposition (DVD), or electron beam physical vapor deposition (EBPVD).

In certain embodiments, the thermal barrier 302 comprises a ceramic material. In certain embodiments, the thermal barrier 302 comprises a zirconium-oxide based ceramic. In certain embodiments, the thermal barrier 302 comprises an yttria stabilized zirconia. In certain embodiments, the mass percent of yttria oxide in the yttria-stabilized zirconia is about 7 mass percent. In certain embodiments the yttria oxide in the yttria-stabilized zirconia is 3 to 20 mass percent.

In certain embodiments, the thermal barrier 302 comprises a yttria stabilized zirconia (comprising 7 mass percent yttria oxide) and has a thermal conductivity between about 0.1 $W \cdot m^{-1} \cdot K^{-1}$ to about 10 $W \cdot m^{-1} \cdot K^{-1}$ and a thickness between about 0.25 mm (0.01 inches) to about 1.52 mm (0.06 inches).

In some embodiments, the thermal barrier 302 remains stable at temperatures of up to about 1700 K. If the temperature of the thermal barrier 302 is 1700 K or below, the thermal barrier 302 can withstand steady state reactor conditions. In other embodiments, the thermal barrier 302 remains stable at temperatures exceeding 1700 K.

A binder 304 is used to adhere thermal barrier 302 with the inner cooling channel wall 306 (i.e., the substrate). In certain embodiments, the binder 304 comprises a metal. In certain embodiments, the binder 304 comprises an alloy of copper and has between about 10 units and 150 units of thermal conductivity ($W \cdot m^{-1} \cdot K^{-1}$). In certain embodiments, the binder 304 comprises an oxide.

In certain embodiments, the binder 304 comprises a metallic bond coat layer in contact with the inner cooling channel wall 306 and a thermally grown oxide in contact with the metallic bond coat and the thermal barrier 302.

In certain embodiments, the binder 304 has a thickness of about 1.02 mm (0.04 inches). In certain embodiments, the binder 304 has a thickness of greater than about 1.02 mm (0.04 inches).

In certain embodiments, the inner cooling jacket wall 306 comprises a copper alloy and has a thermal conductivity between about 10 $W \cdot m^{-1} \cdot K^{-1}$ to greater than about 350 $W \cdot m^{-1} \cdot K^{-1}$. In certain embodiments, the inner cooling jacket wall has a thickness of at least about 1.27 mm (0.05 inches). In certain embodiments the inner cooling jacket wall has a thickness of less than 0.1 inches in another embodiment the inner cooling jacket wall has a thickness less than 0.25 inches and in another embodiment the cooling channel wall has a thickness less than 0.5 inches.

In certain embodiments the inner cooling channel wall and the outer cooling jacket wall are constructed of the same material. In certain embodiments, the outer reactor wall is constructed of the same material as the inner cooling jacket wall or the outer cooling jacket wall. In certain embodiments, a coolant is introduced into the coolant channel 308 at inlet 312. In certain embodiments, the coolant flows in a direction opposite to that of the combustion gas stream in the reactor. The coolant effluent flows out of the coolant channel 310 at outlet 314.

In certain embodiments, the coolant comprises water. In various embodiments, the coolant comprises hydrogen or a hydrocarbon. In various embodiments, the coolant comprises one or more of the components of the fuel that is fed into the fuel injection zone 108. In certain embodiments, the fuel mixture is circulated through the cooling channel 308 before being fed into the fuel injection zone 108. In certain embodiments, water is circulated through the cooling channel 308. The cooling effluent then exits outlet 314 as steam, which is subsequently fed into the fuel injection zone through inlet 104 (visible in FIG. 1) to act as the bulk of the combustion gas stream.

In some embodiments, a thermal insulation layer 318 is disposed over the reactor wall 316. In various embodiments, the thermal insulation layer 318 comprises foam insulation, aerogels, microporous silica, ceramic fiber insulation, zirconia fiber insulation, perlite insulation, calcium silicate insulation, fiberglass, or a combination thereof.

Figure 4A:
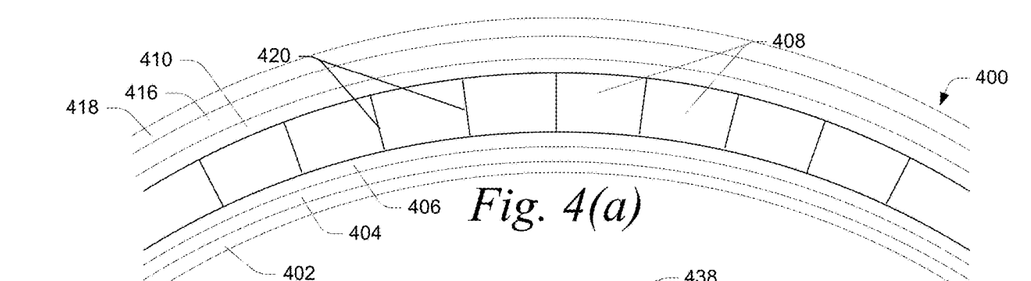
FIG. 4(a)-4(c) are views of a portion of a transverse cross section of various embodiments of a pyrolitic reactor.

Referring to FIG. 4(a), a transverse cross section 400 of certain embodiments of a cooled reactor wall (i.e., the sidewall of the combustion zone) along section line A-A in FIG. 1 is depicted. A thermal barrier 402 is adhered to the cooling jacket inner wall 406 by a binder 404. A cooling jacket outer wall 410 is disposed over the cooling jacket inner wall 406. In certain embodiments, the space between the cooling jacket inner wall 406 and the cooling jacket outer wall 410 is divided into a plurality of channels 408 by baffles 420. In certain embodiments, the baffles are constructed from the same material as the cooling jacket inner wall 406. In another embodiment, the space between the cooling jacket inner wall 406 and the cooling jacket outer wall 410 is a single channel (i.e., the channel is not divided into a plurality of channels by baffles). As the coolant flows through the channels 408, it carries away heat from the cooling jacket inner wall 406.

In some embodiments (not shown), the channels 408 are tubes. In some embodiments (not shown), the channels are embedded directly within the wall of a thick-walled reactor.

In various embodiments, the cooling jacket inner wall 406 comprises a material with a thermal conductivity of at least about 200 $W \cdot m^{-1} \cdot K^{-1}$. In certain embodiments, the outer reactor wall 406 comprises a material with a thermal conductivity of about 350 $W \cdot m^{-1} \cdot K^{-1}$. In certain embodiments, the cooling jacket inner wall 406 comprises a material with a thermal conductivity greater than about 350 $W \cdot m^{-1} \cdot K^{-1}$. In various embodiments, the cooling jacket inner wall 406 comprises copper, nickel, tungsten, hafnium, rare earth metals, hafnium carbide, carbide formations of other metals, or combinations or alloys thereof.

In certain embodiments, wherein baffles 420 are not used, the thermal barrier 402 is about 0.5 mm (0.02 inches) thick, the binder 404 is about 0.2 mm thick (0.01 inches), the cooling jacket inner wall 406 is about 10 mm (0.39 inches) thick, the cooling channel 308 is about 8 mm (0.31 inches) thick, the cooling jacket outer wall 410 is about is about 10 mm (0.39 inches) thick, the outer reactor wall 416 is about 10 mm (0.39 inches) thick, and the insulation 418 is about 75 mm (2.95 inches) thick.

In certain embodiments, wherein baffles 420 are used, the thermal barrier 402 is about 0.5 mm (0.02 inches) thick, the binder 404 is about 0.2 mm (0.01 inches) thick, the cooling jacket inner wall 406 is about 3 mm (0.12 inches) thick, the cooling channel 308 is about 8 mm (0.31 inches) thick, the cooling jacket outer wall 410 is about is about 3 mm (0.12 inches) thick, the outer reactor wall 416 is about 25 mm (0.98 inches) thick, and the insulation 418 is about 100 mm (3.94 inches) thick.

Figure 4B:
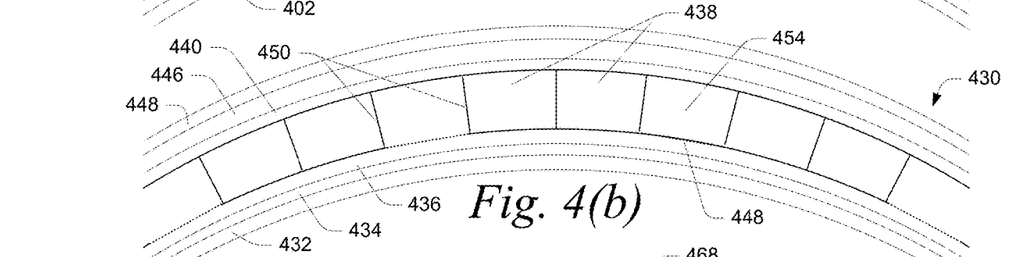

Referring to FIG. 4(b), a transverse cross section 430 of another embodiment of a cooled reactor wall along section line A-A in FIG. 1 is depicted. A thermal barrier 432 is adhered to the cooling jacket inner wall 436 by a binder 434. A cooling jacket outer wall 440 is disposed over the cooling jacket inner wall 436. The space between the cooling jacket outer wall 440 and the cooling jacket inner wall 436 is divided into a plurality of channels 438 and 454 by baffles 440.

The cooling jacket inner wall 436 is formed to include a plurality of perforations 452 extending therethrough along a portion of the channels 438 and 454. In this embodiment, the binder 434 and the thermal barrier 432 are porous. As such, the channel 454 is in fluid communication with the interior of the reactor 100.

As coolant flows through the channels 438, it carries away heat from the cooling jacket inner wall 406. As the coolant flows through the perforated channels 454, a portion of the coolant migrates through the binder 434 and the thermal barrier 432 and enters the reactor. In some embodiments, the high temperature and high velocity of the combustion gas stream within the reactor causes the coolant to form a film on the interior walls of the reactor. This film absorbs the convective heat flux along the interior surface of the reactor and thereby reduces the amount of heat that is absorbed into the thermal barrier 432. As the coolant is transported downstream by the movement of the combustion gas stream, additional coolant is provided from the channel 454, thereby achieving steady state operation. This type of cooling, i.e., flowing coolant through a porous surface to form a thin film of coolant over the surface to be cooled, is known as transpiration cooling. In addition to forming a film over the interior surface of the reactor, the flow of coolant through porous layers 432 and 434 is very effective in removing heat from the cooling jacket inner wall 436, the binder 434 and the thermal barrier 432.

In certain embodiments (not shown), the perforations 452 in the cooling jacket inner wall 436 extend through the binder 434 and the thermal barrier 432. In this embodiment, the binder 434 and the thermal barrier 432 need not be porous. The coolant in channel 454 is in direct fluid communication with the interior of the reactor via the perforations 448. This type of cooling, i.e., flowing the coolant through small holes to form a thin film of coolant over the surface to be cooled, is known as film cooling.

Figure 4C:
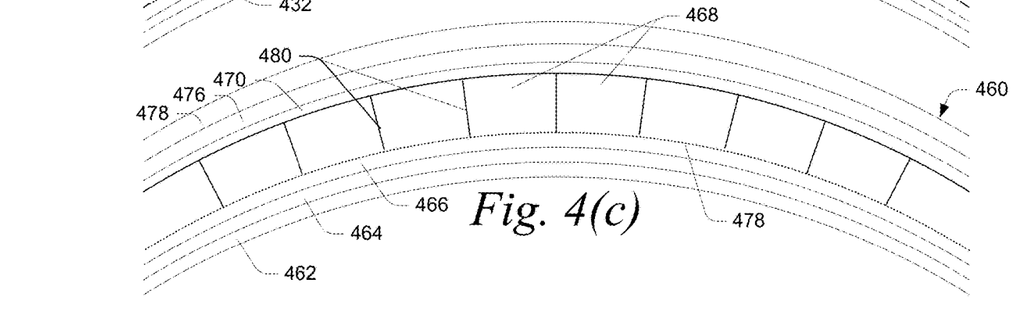

Referring to FIG. 4(c), a transverse cross section 460 of yet another embodiment of a cooled reactor wall along section line A-A in FIG. 1 is depicted. A thermal barrier 462 is adhered to the cooling jacket inner wall 466 by a binder 464. A cooling jacket 468 is disposed over the cooling jacket inner wall 466. The space between the cooling jacket 468 and the cooling jacket inner wall 466 is divided into a plurality of channels 468 by a plurality of baffles 480.

In certain embodiments, cooling jacket inner wall 466 is formed to include a plurality of perforations 482 under all channels 468. In certain embodiments, the binder 434 and the thermal barrier 432 are porous. As coolant flows through the channels 468, it cools by two modes. First, the bulk flow of the coolant pulls heat from the cooling jacket inner wall 466. Second, a portion of the coolant migrates through the porous layers 462 and 464 and enters the interior of the reactor, resulting in transpiration cooling.

In another embodiment (not shown), the cooling jacket inner wall 466, the binder 464 and the thermal barrier 462, are formed to include a plurality of perforations 482 extending therethrough. In this embodiment, the binder 464 and the thermal barrier 462 need not be porous. The coolant in channels 468 is in direct fluid communication with the interior of the reactor via the perforations 482, resulting in film cooling.

In some embodiments (not shown), the interior of channels 454 in FIG. 4(b) and channels 468 in FIG. 4(c) are coated with an insulator having a thermal conductivity of less than 0.5 $W \cdot m^{-1} \cdot K^{-1}$.

In various embodiments, the cooling jacket inner wall 436 and 466 comprise a material with a thermal conductivity between about 10 $W \cdot m^{-1} \cdot K^{-1}$ to about 200 $W \cdot m^{-1} \cdot K^{-1}$. In various embodiments, the cooling jacket inner wall 436 and 466 comprise stainless steel grade 304 or 316.

In some embodiments, the cooling system is configured to direct coolant for film or transpiration cooling into the reactor along the entire length of the cooling jacket 308 (in FIG. 3). In other embodiments, the cooling system is configured to direct coolant for film or transpiration cooling into the reactor at specific locations along the longitudinal length of the reactor. In certain embodiments, the cooling system is configured to direct coolant for film or transpiration cooling into the reactor at a single location near the inlet 312 (in FIG. 3).

Figure 5:
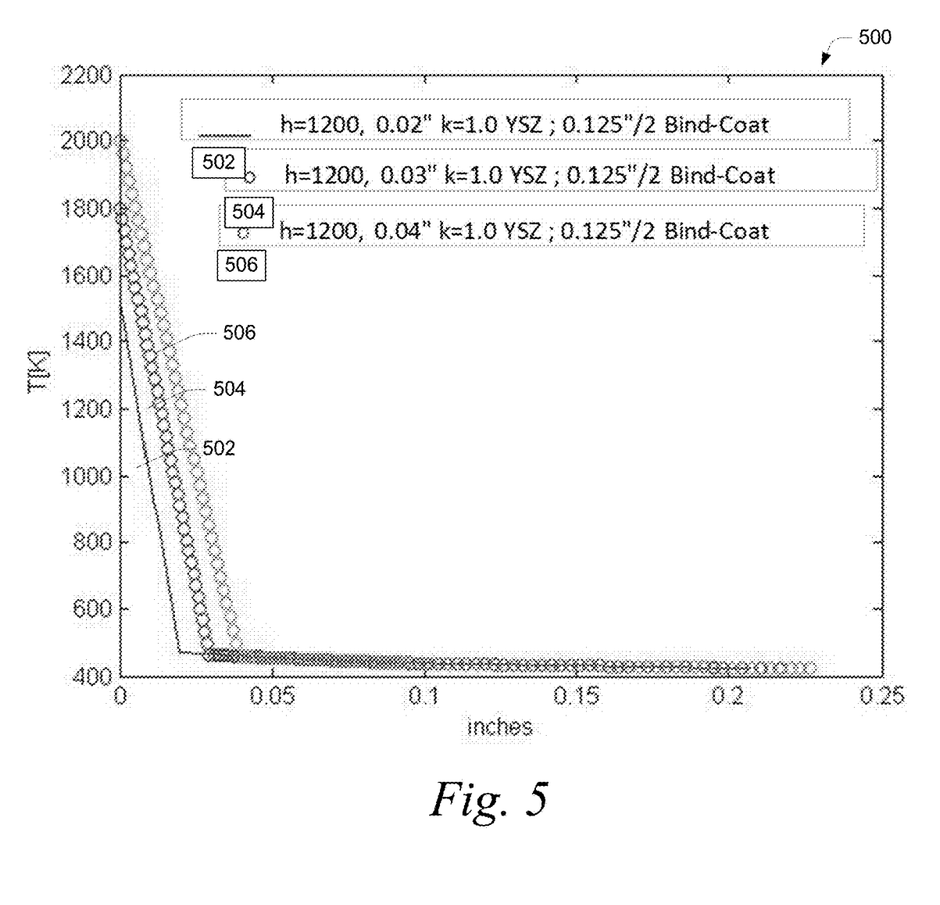
FIG. 5 is a graph showing the temperature profile for various embodiments of an actively cooled reactor wall.

Referring to FIG. 5, a graph 500 showing the temperature profile for various embodiments of an actively cooled reactor wall is depicted. The graph represents the temperature (y-axis) across the thickness of the cooled reactor wall (x-axis), which includes the cooling jacket inner wall, the thermal barrier, and the binder and where 0 on the x-axis represents the interior surface of the cooling jacket inner wall. Curves 502, 504, and 506 represent a reactor wall having an yttria-stabilized zirconia thermal barrier having a thermal conductivity of 1 and a thickness of 0.51 mm (0.02 inches), 1.02 mm (0.04 inches), and 1.52 mm (0.06 inches), respectively. The thermal barrier is adhered to the cooling jacket inner wall with a binder having a thickness of 1.59 mm (0.0625 inches), and a cooling jacket inner wall thickness of 3 mm (0.12 inches).

For the graph 500, the reactor wall was configured as depicted in FIG. 4(a). Water was used as the coolant and all water within the channels 408 was converted into steam. The water was circulated at a rate of between about 10%-20% of that of the methane feedstock flowed into the reactor via the feedstock injectors. The thermal barrier was adhered to the cooling jacket inner wall with a binder having a thickness of 1.59 mm (0.0625 inches).

The surface temperature for the thermal barrier of 0.51 mm (0.02 inches) (curve 502) is below 1700 K, whereas surface temperatures for thermal barrier thicknesses 0.76 (0.03 inches) (curve 504) and 1.02 mm (0.04 inches) (curve 506) are above 1700 K. In some embodiments, it is desirable to maintain the surface temperature at or below 1700 K to maximize the life of the thermal barrier.

Figure 6:
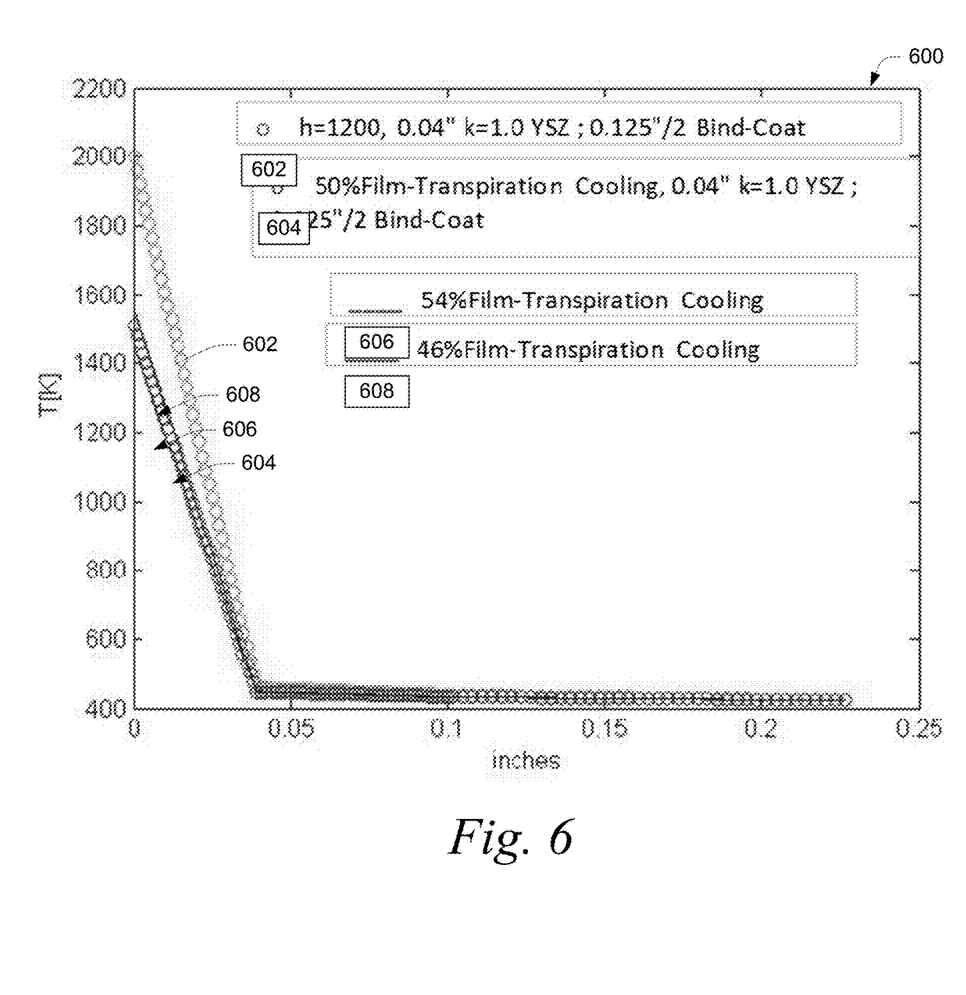
FIG. 6 is a graph showing the temperature profile for various embodiments of an actively cooled reactor wall employing transpiration or film cooling.

Referring to FIG. 6, a graph 600 showing the temperature profile for various embodiments of an actively cooled reactor wall using transpiration or film cooling is depicted. The graph represents the temperature (y-axis) across the thickness of the cooled reactor wall (x-axis), which includes the cooling jacket inner wall, the thermal barrier, and the binder and where 0 on the x-axis represents the interior surface of the cooling jacket inner wall. Curve 602 represents a reactor wall having an yttria-stabilized zirconia thermal barrier having a thermal conductivity of 1 and a thickness of 1.02 mm (0.04 inches) that removes heat by indirect cooling (i.e., heat travels across the thermal barrier and binder, where it is absorbed into the coolant and carried away). Curves 604, 606, and 608 represent a reactor wall having an yttria-stabilized zirconia thermal barrier having a thermal conductivity of 1 and a thickness of 1.02 mm (0.04 inches) and employing 50%, 54%, and 46% film or transpiration cooling, respectively. For purposes of clarity, the 50%, 54% and 46% values signify the percent of the total amount of heat removed that is removed by film or transpiration cooling, respectively, with the balance being removed by indirect cooling.

In various embodiments, the desired percentage of cooling accomplished by film/transpiration cooling (as a percentage of total cooling) is selected by the choice of reactor geometry, cooling channel(s) geometry, system layout (for instance the location and number of perforations and/or porosity of the thermal barrier), and/or the flow rate of coolant through the cooling channel(s).

For the graph 600, the reactor wall was configured as depicted in FIG. 4(b) or FIG. 4(c). Water was used as the coolant and all water within the channels 408 was converted into steam. For line 602, the coolant was circulated at a rate of between about 5%-40% of that of the methane feedstock flowed into the reactor via the feedstock injectors. The thermal barrier was adhered to the cooling jacket inner wall with a binder having a thickness of 1.59 mm (0.0625 inches).

The surface temperature without film or transpiration cooling (curve 602) was significantly higher than that with film or transpiration cooling (curve 604, 606, or 608). As a result, film or transpiration cooling enables the use of a much thicker thermal barrier, which in some embodiments has a longer operational life than thinner thermal barriers.

In various embodiments, between about 10% to about 40% of the coolant enters the reactor through pores (transpiration cooling) or holes (film cooling). In certain embodiments, 30% of the coolant enters the reactor through pores (transpiration cooling) or holes (film cooling).

The invention claimed is:
1. A method to produce acetylene, comprising:
introducing a fuel and oxygen into a fuel injection zone;
combusting said fuel and oxygen in a combustion zone to create a combustion gas stream;
cooling a sidewall of said combustion zone, wherein said cooling comprises flowing a coolant through at least one channel in said sidewall, wherein a portion of said coolant enters, via pores, said combustion zone through said sidewall;

accelerating the combustion gas stream and the portion of the coolant to supersonic speed in an expansion zone;

injecting feedstock into the combustion gas stream in a feedstock injection zone; and reacting the feedstock to produce acetylene.

2. The method of claim 1, further comprising injecting said coolant into said fuel injection zone.

3. The method of claim 1 further comprising heat protecting the combustion zone by surrounding the combustion zone with a thermal barrier.

4. The method of claim 1 wherein the fuel and the oxygen are mixed prior to introducing into the fuel injection zone.

5. The method of claim 1 further comprising a carrier gas introduced into the fuel injection zone.

6. The method of claim 5 wherein the carrier gas comprises at least one of water, a hydrocarbon, hydrogen, carbon monoxide, carbon dioxide, a promoter, a corrosion inhibitor, nitrogen, a noble gas, or combinations thereof.

7. The method of claim 1 wherein the feedstock comprises methane.

8. The method of claim 1 further comprising creating a shockwave and using the shockwave to heat the feedstock and combustion gas stream after the feedstock injection zone.

9. The method of claim 1 further comprising creating a shock train and using the shock train to heat the feedstock and combustion gas stream after the feedstock injection zone.

10. The method of claim 1 further comprising quenching the acetylene.

11. The method of claim 10 wherein the quenching comprising spraying the acetylene with water.

* * * * *